(12) United States Patent
Nollert et al.

(10) Patent No.: US 7,610,943 B2
(45) Date of Patent: Nov. 3, 2009

(54) SYSTEMS AND METHODS FOR DISPENSING PORTIONS OF VISCOUS MATERIAL

(75) Inventors: Peter Nollert, Bainbridge Island, WA (US); Alexandrina Muntianu, Bellevue, WA (US); Robert C. Haushalter, Los Gatos, CA (US); Dean Allyn Hopkins, Jr., San Jose, CA (US)

(73) Assignee: Emerald Biosystems, Inc., Bainbridge Island, WA (US)

( * ) Notice: Subject to any disclaimer, the term of this patent is extended or adjusted under 35 U.S.C. 154(b) by 444 days.

(21) Appl. No.: 11/149,855

(22) Filed: Jun. 8, 2005

(65) Prior Publication Data

US 2006/0043103 A1 Mar. 2, 2006

Related U.S. Application Data

(60) Provisional application No. 60/578,724, filed on Jun. 10, 2004.

(51) Int. Cl.
*B65B 1/04* (2006.01)
*B67D 5/60* (2006.01)
*G01N 21/00* (2006.01)

(52) U.S. Cl. .............. 141/107; 141/9; 141/27; 141/105; 141/130; 222/145.1; 222/373; 222/395; 422/82

(58) Field of Classification Search .............. 141/2, 141/9, 25–27, 94, 100–107, 130; 222/135, 222/145.1, 145.7, 310, 330, 373, 395; 604/82, 604/191, 240; 436/53, 180; 422/82, 100
See application file for complete search history.

(56) References Cited

U.S. PATENT DOCUMENTS

| | | | |
|---|---|---|---|
| 3,731,850 A * | 5/1973 | Weitzel et al. | 222/630 |
| 3,871,826 A | 3/1975 | Bakay | |
| 3,960,187 A * | 6/1976 | Stock et al. | 141/1 |
| 4,333,454 A * | 6/1982 | Hargest, III | 604/28 |
| 4,631,055 A * | 12/1986 | Redl et al. | 604/82 |
| 4,942,998 A * | 7/1990 | Horvath et al. | 228/102 |
| 5,887,755 A * | 3/1999 | Hood, III | 222/135 |
| 6,485,980 B1 | 11/2002 | Adolfsen | |
| 6,723,067 B2 * | 4/2004 | Nielson | 604/82 |
| 6,790,328 B2 * | 9/2004 | Jacobson et al. | 204/453 |
| 6,972,005 B2 * | 12/2005 | Boehm et al. | 604/191 |
| 2002/0072703 A1 | 6/2002 | Nollert et al. | |
| 2004/0092034 A1 | 5/2004 | Nollert et al. | |
| 2004/0096364 A1 | 5/2004 | Nollert et al. | |
| 2004/0163730 A1 | 8/2004 | Olson et al. | |

* cited by examiner

*Primary Examiner*—Timothy L Maust
(74) *Attorney, Agent, or Firm*—Christensen O'Connor Johnson Kindness PLLC

(57) ABSTRACT

Systems and methods are provided for dispensing portions of viscous material, such as the viscous materials used to form crystals of membrane proteins or soluble proteins. A liquid under pressure is used to divide the viscous materials into portions. The divided viscous material portions can optionally be deposited into are receptacle.

13 Claims, 1 Drawing Sheet

SYSTEMS AND METHODS FOR DISPENSING PORTIONS OF VISCOUS MATERIAL

CROSS-REFERENCE TO RELATED APPLICATION

This application claims the benefit of U.S. Provisional Patent Application No. 60/578,724, filed Jun. 10, 2004.

FIELD OF THE INVENTION

The present invention relates to dispensing sized portions of viscous materials. More particularly, the present invention relates to dispensing sized portions of lipid mesophase material for the purpose of generating samples for protein crystallization.

BACKGROUND OF THE INVENTION

Viscous materials, such as gels and lipidic mesophases, including lipidic cubic phases (LCP), have been used successfully for the crystallization of proteins, including integral membrane proteins. The latter are typically very hydrophobic, and tend to aggregate amorphously instead of forming well-ordered three-dimensional crystals. In the practice of the LCP technique, a protein sample is mixed with a lipid to form a gel-like material of protein and lipid. The lipid portion of this material forms a cubic, three-dimensional, lattice which may promote formation of three-dimensional membrane protein crystals.

Crystallization conditions are not known initially, and so typically many crystallization experiments are prepared in an array format, such as in the wells of a 96-well plastic plate. A portion of prepared LCP material, containing the protein and lipid, is dispensed into each reservoir. The LCP material typically remains as a distinct, separate, phase from the aqueous crystallization solution during the crystallization experiment. Membrane protein crystals may be found within the LCP or in the dissolved lipid remnants. Protein crystals of soluble protein may be found anywhere within the crystallization space.

A problem associated with LCP-based crystallization experiments is that lipidic mesophase materials, and viscous LCP in particular, are difficult to dispense accurately. For example, a small portion of the LCP (e.g., 200 nL), is extruded with the aid of a syringe through a needle that is placed onto the surface of the well. The physical continuity of the LCP material has to be disrupted in order to dispense multiple portions of LCP material. In principle, this may be done, for example, by retracting the dispensation needle and thus breaking off a portion of the LCP. For this to occur the LCP has to be attached to a surface so that, when the dispensing needle is retracted, the LCP material adheres to the surface and a portion breaks off as the needle is withdrawn. Such strong bonding between the LCP and the surface material requires sufficient friction at the material interfaces. Sufficient friction is often not present, especially when the surface is not dry. Indeed, in order to prevent dehydration of the LCP material, the surface may be wet with a lubricating liquid. Even when LCP is dispensed onto a dry surface, slight dehydration of the LCP can induce lipid phase transition to form lamellar phases which create a lubricating layer between the surface and the bulk of the LCP material.

If the LCP does not break when the depositing needle is withdrawn, either no LCP material is deposited on the surface, or a variable amount of LCP is deposited in different wells, thereby introducing an additional variable in the protein crystallization experiment.

SUMMARY OF THE INVENTION

The present invention provides systems and methods for dispensing portions of viscous material, such as the viscous materials used to form crystals of membrane proteins. A liquid under pressure is used to divide the viscous material into portions. The viscous material can be divided into portions that each have a desired volume. The systems and methods of the invention facilitate reliable, accurate, division of viscous material into portions.

Thus, in one aspect, the present invention provides systems for dispensing portions of a viscous material. The systems of this aspect of the invention each include: (a) a first dispenser; (b) a second dispenser; and (c) a branched conduit connected to both the first dispenser and the second dispenser, wherein, in operation, a viscous material is introduced into the conduit from the first dispenser, a liquid is introduced into the conduit from the second dispenser, wherein the liquid divides the viscous material into portions within the conduit. The portions of viscous material can then be dispensed from the conduit.

In another aspect, the present invention provides methods for dispensing portions of a viscous material, each method comprising the steps of: (a) using a directed stream of liquid to divide a mass of viscous material, disposed within a conduit, to produce a plurality of portions of viscous material; and (b) dispensing the plurality of portions of viscous material from the conduit. The methods of this aspect of the invention can be used, for example, to dispense portions of viscous materials used to form crystals of membrane proteins or soluble proteins.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1:
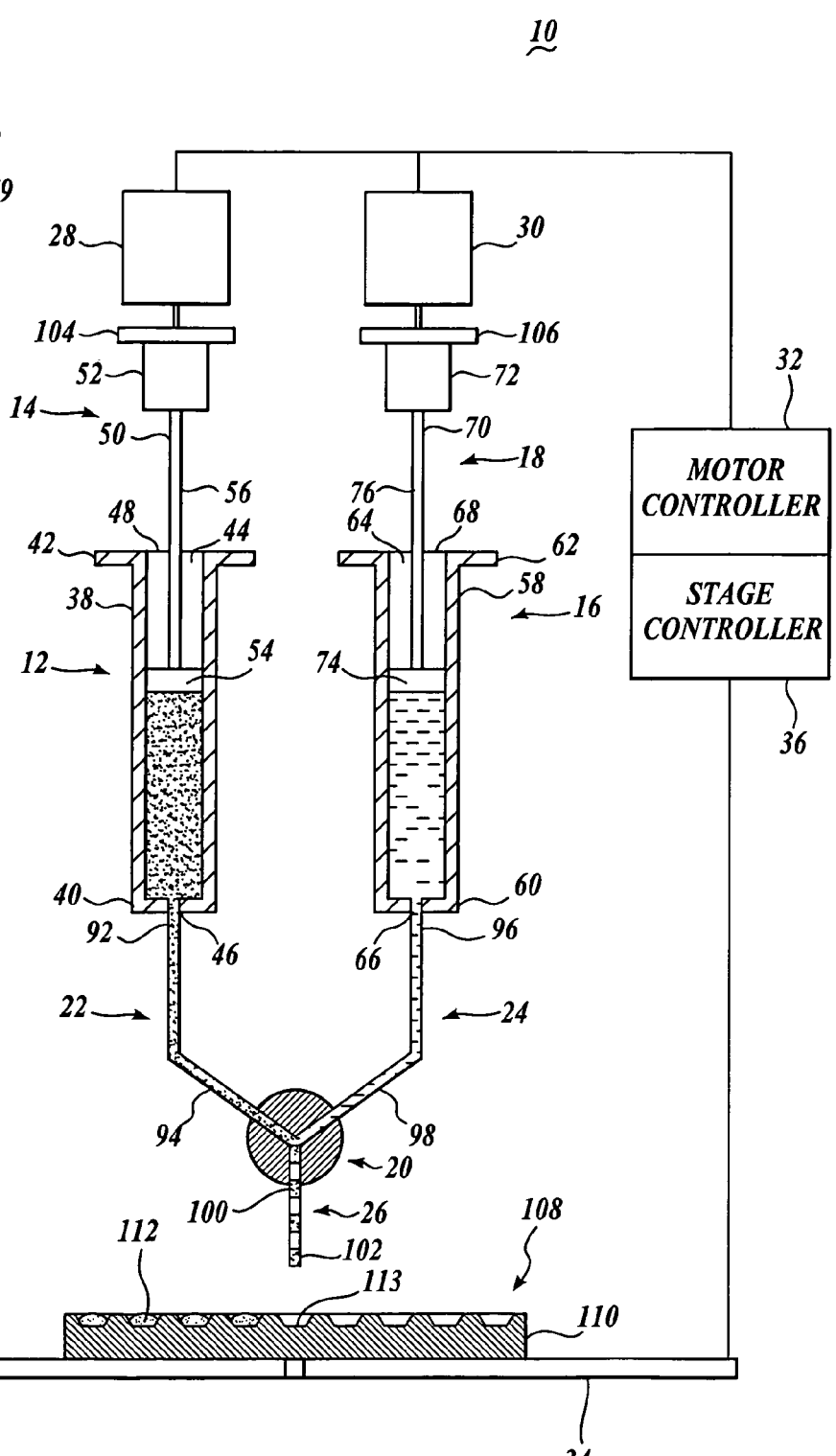
FIG. 1 shows an embodiment of a system of the present invention.

In one aspect, the present invention provides systems for dispensing portions of a viscous material. The systems of this aspect of the invention each include: (a) a first dispenser; (b) a second dispenser; and (c) a branched conduit connected to both the first dispenser and the second dispenser, wherein, in operation, a viscous material is introduced into the conduit from the first dispenser, a liquid is introduced into the conduit from the second dispenser, wherein the liquid divides the viscous material into portions within the conduit. The portions of viscous material can then be dispensed from the conduit. The systems of the invention can divide viscous material into multiple portions that each have the same volume or approximately the same volume.

The systems of the invention are useful for dispensing portions of any viscous material, in particular gels and lipidic mesophases (e.g., the lamellar phase, liquid crystalline phase, the fluid isotropic phase, hexagonal phase, and the lipidic cubic phase, such as the Im3m, Pn3m and Ia3d lipidic cubic phases), that are useful for crystallizing soluble proteins and/or membrane proteins. Examples of viscous materials that can be dispensed in portions using the systems of the present invention include oils (e.g., silicone oil, paraffin oil, mineral oil, vaseline), greases, and gels (such as agarose gels or silica gels). By way of more specific example, the viscous materials can be lipidic cubic phases containing 60% monoolein and 40% water (or an aqueous solution), lipidic cubic phases or lipidic mesophases made from monoacylglycerols and an aqueous solution, lipidic cubic phases or lipidic mesophases made from lipids and an aqueous solution, and lipidic cubic phases or lipidic mesophases made from amphiphile compounds and an aqueous solution. The aqueous solution component of the foregoing, exemplary, viscous materials may contain, for example, detergent-solubilized membrane proteins, soluble proteins, suspended membranes, detergent (e.g., beta-octyl glucoside, dodecylmaltoside), salt, small molecule additives (e.g., glycerol), polymer (polyethyleneglycol), and other compounds used in preparations of membrane proteins.

By way of example, systems of the present invention can dispense portions of a viscous material, wherein the portions have a volume of from 0.1 nL to 500 nL (such as a volume of from 10 nL to 500 nL, or such as a volume of from 1 nL to 100 nL, or such as a volume of from 20 nL to 60 nL). The volume of the portions of viscous material dispensed from a system of the invention can be controlled, for example, by reducing the inner diameter of the conduit to obtain a smaller portion volume.

The systems of the invention can dispense portions of a viscous material at a desired rate. For example, the systems of the invention can dispense a portion of viscous material once during each time interval of a series of successive time intervals, wherein each time interval of the series of successive time intervals is between 100 milliseconds to 10 seconds.

Any liquid can be used to divide the viscous material into portions. For example, water, aqueous solutions, organic solvents and oils can be used to divide the viscous material into portions. By way of more specific example, pure water, pH-buffered water, mixtures of water with glycerol or organic solvents that mix with water (e.g., methanol, ethanol, isopropanol, acetone) can be used to divide the viscous material into portions. If it is desired to form a lipidic cubic phase in the viscous material, then the liquid preferably does not destroy the integrity of the lipidic cubic phase when the liquid contacts the viscous material.

The first and second dispensers can be any container that is sized to contain a desired amount of viscous material or liquid, that includes an entry aperture and an exit aperture, and which is configured to permit pressure to be applied to the liquid or viscous material within the dispenser to force the liquid or viscous material out of the dispenser. The dispenser should not chemically react with the liquid or viscous material disposed therein. Examples of useful dispensers include positive displacement syringes, such as positive displacement syringes made from plastic or glass. Suitable syringes can typically withstand internal pressures (generated within the systems of the invention in order to move the viscous material through the system) of greater than 500 psi. By way of example, syringes having a volume of from 10 µl to 500 µl (e.g., a volume of 10 µl, 25 µl, 50 µl, 100 µl, 250 µl, or 500 µl) are suitable for use in the systems of the present invention (e.g., the 1700 RN Series GASTIGHT syringes, available from Hamilton Company, 4970 Energy Way, Reno, Nev. 89502, USA).

The branched conduit is hollow and can be made from any material that is strong enough to withstand the pressure of the liquid and viscous material within the conduit, and that does not chemically react with the viscous material or the liquid. The branched conduit can be formed from a single piece of material (such as a single piece of metal tubing), or can be made from several pieces of material (e.g., several portions of metal tubing that are screwably connected to each other. For example, the conduit can be made from metal tubing, or from a needle (e.g., steel needle RN22GA from Hamilton Company, 4970 Energy Way, Reno, Nev. 89502, USA), or from a glass or teflon capillary. For example, the inner diameter of the conduit can be in the range of from 0.001 inches to 0.016 inches (such as from 0.0045 inches to 0.016 inches). For example, the outer diameter of the conduit can be in the range of from 0.028 inches to 0.185 inches.

In some embodiments, the systems of the present invention include a splitter that divides the conduit into a first segment that connects the first dispenser to the splitter, and also divides the conduit into a second segment that connects the second dispenser to the splitter. The splitter includes a first entry port (e.g., a threaded entry port) that engages an end of the first segment of the conduit, and a second entry port (e.g., a threaded entry port) that engages an end of the second segment of the conduit. The splitter also includes an exit port which permits the portions of viscous material to leave the splitter. In some embodiments, the splitter further divides the conduit into a third segment that engages the splitter exit port and that directs portions of the viscous material out of the splitter. The third segment can, for example, screwably engage a threaded exit port of the splitter. The splitter defines an internal channel having at least two portions (more typically three portions) that directs the flow of liquid and viscous material within the splitter.

Examples of useful splitters include the 1/32-inch Microvolume connector Y-type (0.15 mm bore, made from stainless steel, product number MY.5XCS6) manufactured by Valco Instruments Co. Inc., 7806 Bobbitt, Houston, Tex. 77055. Other useful splitters manufactured by Valco Instruments Co. Inc., include product number MY.5XCTI (made from Titanium) and product number MY.5XCHC.

The first and second dispensers can be actuated, for example, by a first motor, and a second motor, respectively in order to express viscous material or liquid from the dispensers. Thus, for example, in embodiments of the systems wherein the first and second dispensers are syringes, the plungers of the syringes may be separately engaged by motors to express viscous material and liquid therefrom. Again by way of example, the viscous material and liquid may be manually expressed from the first and second dispensers, respectively.

Portions of viscous material dispensed from the system of the present invention are typically dispensed into a receptacle, such as into the wells of a crystallization plate, such as a 72-well, 96-well, 384 well, or 1536 well plate. Crystallization plates are available, for example, from deCODE biostructures, 7869 NE Day Road West, Bainbridge Island, Wash. 98110, USA, or from Hampton Research, 34 Journey, Aliso Viejo, Calif. 92656-3317, U.S.A., or from Corning, One Riverfront Plaza, Corning, N.Y. 14831, USA (e.g., the Corning 96 Well crystallization Plate™).

To facilitate dispensing numerous portions of viscous material into receptacles, the receptacle(s) can be supported on a moveable base which is actuated by a motor under the control of a computer program, and that moves individual receptacles (such as the wells of a 96-well plate) under the portion of the conduit that directs portions of viscous material out of the splitter. The movable base typically can move up, down, and sideways.

FIG. 1 shows a drawing of a representative system 10 of the present invention. In brief, system 10 includes a first dispenser 12, a first dispenser plunger 14 seated within first dispenser 12 for dispensing a viscous material from first dispenser 12, a second dispenser 16, and a second dispenser plunger 18 seated within second dispenser 16 for dispensing a liquid from second dispenser 16. System 10 also includes a splitter 20, a first conduit section 22, a second conduit section 24, and a third conduit section 26. First conduit section 22 connects first dispenser 12 to splitter 20, second conduit section 24 connects second dispenser 16 to splitter 20, and third conduit section 26 directs portions of viscous material out of splitter 20. System 10 also includes a first motor 28 that actuates first plunger 14, and a second motor 30 that actuates second plunger 18. First motor 28 and second motor 30 are controlled by a motor controller software program 32. System 10 also includes a movable stage 34 that is controlled by a stage controller software program 36.

Considering the components of system 10 in more detail, first dispenser 12 includes a body 38 defining a first end 40, a second end 42, and a cavity 44. First end 40 defines an opening 46. Second end 42 also defines an opening 48, that is larger than first end opening 46, and that receives first dispenser plunger 14.

First dispenser plunger 14 comprises a body 50 that defines a first end 52, a second end 54, and an intermediate section 56 that connects plunger first end 52 and plunger second end 54.

Second dispenser 16 includes a body 58 defining a first end 60, a second end 62, and a cavity 64. First end 60 defines an opening 66. Second end 62 also defines an opening 68, that is larger than first end opening 66, and that receives second dispenser plunger 18.

Second dispenser plunger 18 comprises a body 70 that defines a first end 72, a second end 74, and an intermediate section 76 that connects plunger first end 72 and plunger second end 74.

Figure 2:
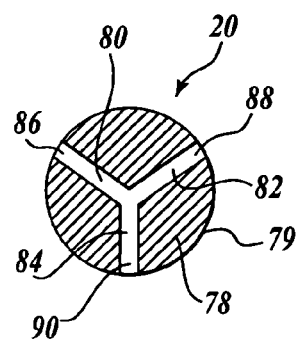
FIG. 2 shows a cross section of a splitter used in the system shown in FIG. 1.

As shown in the cross-section of splitter 20 shown in FIG. 2, splitter 20 includes a splitter body 78 that defines an external surface 79, a channel first portion 80, a channel second portion 82, and a channel third portion 84 that together form a Y-shape. Channel first portion 80 opens onto external surface 79 through a first opening 86, channel second portion 82 opens onto external surface 79 through a second opening 88, and channel third portion 84 opens onto external surface 79 through a third opening 90.

Turning again to FIG. 1, first conduit section 22 includes a first end 92 that engages first end opening 46 of first dispenser 12, and a second end 94 that engages first opening 86 of splitter 20. Second conduit section 24 includes a first end 96 that engages first end opening 66 of second dispenser 16. Second conduit section 24 includes a second end 98 that engages second opening 88 in splitter 20. Third conduit section 26 includes a first end 100, that engages third opening 90 of splitter 20, and a second end 102 from which portions of viscous material emerge.

The exemplary system illustrated in FIG. 1 also includes a first plunger actuating member 104, that engages first plunger 14, and a second plunger actuating member 106 that engages second plunger 18. First plunger actuating member 104 is actuated by first motor 28, and second plunger actuating member 106 is actuated by second motor 30.

A crystallization plate 108 (shown in cross-section in FIG. 1) is disposed on moveable stage 34. Plate 108 includes a plate body 110 that defines multiple wells 112, wherein each well includes a well surface 113.

Figure 3:
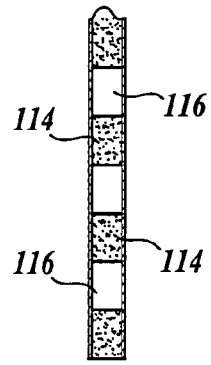
FIG. 3 shows a longitudinal cross-section of a portion of a conduit containing alternating portions of viscous material and liquid.

In operation, first motor 28 actuates first plunger actuating member 104 that depresses first dispenser plunger 14, thereby applying pressure to viscous material within cavity 44 of first dispenser 12, and expelling an amount of viscous material from first dispenser 12 into first conduit section 22. Second motor 30 actuates second plunger actuating member 106 which depresses second plunger 18, thereby applying pressure to liquid within cavity 64 of second dispenser 16, and expelling an amount of liquid from cavity 64 into second conduit section 24. Viscous material enters channel first portion 80, of splitter 20, from first conduit section 22 and proceeds into channel third portion 84. Liquid enters channel second portion 82, of splitter 20, from second conduit section 24 and engages the viscous material, thereby dividing the viscous material into portions 114. As shown more clearly in FIG. 3, viscous material portions 114 within channel third portion 84 are separated by liquid portions 116. Viscous material portions 114 emerge from third conduit portion second end 102 and are deposited onto well surface 113 of plate 108. Plate 108 is moved by movable stage 34 in order to position well surface 113 under third conduit section second end 102. In order to deposit viscous material portions 114 onto well surface 113, third conduit portion second end 102 is positioned close to (but not touching) well surface 113. A viscous material portion 114, together with a portion of liquid 116, is extruded from third conduit portion second end 102 onto well surface 113. Movable stage 34 moves plate 108 away from third conduit portion second end 102, so that viscous material portion 114 remains attached to well surface 113 and detaches from third conduit portion second end 102.

First motor 28 and second motor 30 are controlled by motor controller 32, and can be actuated sequentially so as to alternately force a portion of viscous material through first conduit section 22, followed by a portion of liquid through second conduit section 24, thereby dividing the viscous material into portions 114.

In another aspect, the present invention provides methods for dispensing portions of a viscous material, each method comprising the steps of: (a) using a directed stream of liquid to divide a mass of viscous material, disposed within a conduit, to produce a plurality of portions of viscous material; and (b) dispensing the plurality of portions of viscous material from the conduit. The systems of the present invention can be used, for example, to practice the methods of the present invention.

Examples of viscous materials that can be dispensed using the methods of this aspect of the invention are set forth in connection with the systems of the invention. The portions of viscous material can be sized portions (i.e., the portions have a desired size). For example, the portions of viscous material can have a volume of from 0.1 nL to 500 nL (such as a volume of from 10 nL to 500 nL, or such as a volume of from 1 nL to 100 nL, or such as a volume of from 20 nL to 60 nL)

Examples of liquids that can be used to divide the viscous material into portions are set forth in connection with the systems of the invention. Similarly, examples of conduits, and materials for making conduits, useful in the practice of this aspect of the invention are set forth in connection with the systems of the invention.

In the practice of some embodiments of the methods of the invention, a portion of viscous material is dispensed from the conduit once during each time interval of a series of successive time intervals, wherein each time interval of the series of successive time intervals is between 100 milliseconds to 10 seconds.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for dispensing portions of a viscous material, the system comprising:
    (a) a first dispenser;
    (b) a second dispenser; and
    (c) a branched conduit connected to both the first dispenser and the second dispenser, the branched conduit comprising a splitter that divides the branched conduit, the splitter consisting of a first segment that connects the first dispenser to the splitter, a second segment that connects the second dispenser to the splitter, and a third segment leading from the splitter and connected to an exit port for depositing portions of viscous material onto a surface, wherein, in operation, a viscous material is introduced into the splitter from the first dispenser, a liquid is introduced into the splitter from the second dispenser, wherein the liquid divides the viscous material into portions within the splitter, wherein the branched conduit is a hollow tube having a generally circular transverse cross-section, the internal diameter of the conduit is in the range of from 0.001 inch to 0.016 inch, and the first dispenser and the second dispenser provide alternating pressure such that only one of the viscous material and the liquid is forced through the branched conduit at one time.

2. A system of claim 1 wherein the first dispenser is a syringe.

3. A system of claim 1 wherein the second dispenser is a syringe.

4. A system of claim 1 wherein the first dispenser is actuated by a first motor, and the second dispenser is actuated by a second motor.

5. A system of claim 1 further comprising a mobile stage that supports a receptacle that receives a portion of the viscous material from the branched conduit.

6. A system of claim 1 further comprising a controller for controlling operation of the syringes.

7. A system of claim 1 further comprising a controller for controlling operation of the mobile stage.

8. A method for dispensing portions of a viscous material, the method comprising the steps of:
    (a) using a directed stream of liquid provided by a second dispenser to divide a mass of viscous material, provided by a first dispenser and disposed within a branched conduit, to produce a plurality of portions of viscous material, wherein the branched conduit is a hollow tube having a generally circular transverse cross-section comprising a splitter that divides the branched conduit, the splitter consisting of a first segment that connects the first dispenser to the splitter, a second segment that connects the second dispenser to the splitter, and a third segment leading from the splitter and connected to an exit port for depositing portions of viscous material onto a surface, wherein the internal diameter of the conduit is in the range of from 0.001 inch to 0.016 inch, and the first dispenser and the second dispenser provide alternating pressure such that only one of the viscous material and the liquid is forced through the branched conduit at one time; and
    (b) dispensing the plurality of portions of viscous material from the branched conduit.

9. The method of claim 8 wherein the viscous material is selected from the group consisting of gels and lipidic cubic phase material.

10. The method of claim 9 wherein the lipidic cubic phase material comprises a monoalkylglyceride and water.

11. The method of claim 8 wherein the liquid is selected from the group consisting of aqueous solutions, oils, and organic solvents.

12. The method of claim 8 wherein the volume of each portion of the plurality of portions of viscous material is in the range of from about 1 nL to about 10 mL.

13. The method of claim 8 wherein a portion of viscous material is dispensed from the branched conduit once during each time interval of a series of successive time intervals, wherein each time interval of the series of successive time intervals is between 100 milliseconds to 10 seconds.

* * * * *

UNITED STATES PATENT AND TRADEMARK OFFICE
CERTIFICATE OF CORRECTION

PATENT NO. : 7,610,943 B2 Page 1 of 1
APPLICATION NO. : 11/149855
DATED : November 3, 2009
INVENTOR(S) : P. Nollert et al.

It is certified that error appears in the above-identified patent and that said Letters Patent is hereby corrected as shown below:

| COLUMN | LINE | ERROR |
|---|---|---|
| (57) | Abstract | "are" should read --a-- |
| Pg. 1, col. 2 | 6 of text | |

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,610,943 B2 Page 1 of 1
APPLICATION NO. : 11/149855
DATED : November 3, 2009
INVENTOR(S) : Nollert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 957 days.

Signed and Sealed this

Twelfth Day of October, 2010

David J. Kappos
*Director of the United States Patent and Trademark Office*